United States Patent [19]

Kweon

[11] Patent Number: 5,187,124
[45] Date of Patent: Feb. 16, 1993

[54] DISINFECTANT CERAMIC COMPOSITION

[75] Inventor: Young J. Kweon, Seoul, Rep. of Korea

[73] Assignee: Samwoo Far Infra-Red Ray Co., Ltd., Rep. of Korea

[21] Appl. No.: 770,117

[22] Filed: Oct. 2, 1991

[30] Foreign Application Priority Data

Oct. 9, 1990 [KR] Rep. of Korea ............... 90-16729

[51] Int. Cl.$^5$ .................... C09K 3/00; C04B 35/00
[52] U.S. Cl. ........................ 501/1; 106/35; 501/123
[58] Field of Search ............. 501/1, 13, 123; 106/35

[56] References Cited

U.S. PATENT DOCUMENTS 5,009,898  4/1991  Sakuma et al. ............... 106/35

Primary Examiner—Mark L. Bell
Assistant Examiner—Deborah Jones
Attorney, Agent, or Firm—Lieberman & Nowak

[57] ABSTRACT

A disinfectant bio-ceramic material which can be easily manufactured, has a stable disinfectant property, catches heavy metals which are harmful to human body, and radiates far infra-red rays with a positive influence on living things.

Examples of the base materials used are compounds containing alkaline earth metal and phosphorus such as granulated bone, keel (fossils of vertebrate animals), artificial spatite, phosphate calcium ore, TCP (tricalcium phosphate), $Mg_3(PO_4)_2.5H_2O$ $MgO.3SiO_2.xH_2O$ and $Sr(C_3H_5OH)_2.3H_2O$ in which compounds containing calcium and phosphorus are most preferable. With these base materials, by reacting metals with disinfectant and harmless property such as silver, copper, or zinc, a disinfectant bio-ceramic material is obtained.

7 Claims, No Drawings

DISINFECTANT CERAMIC COMPOSITION

BACKGROUND OF THE INVENTION

The present invention relates to a ceramic composition with antibacterial and/or disinfectant properties. More particularly, it is concerned with a ceramic composition manufactured by substituting such disinfectant metals as silver, copper, and zinc with ceramic materials, and a polymer or wall paper manufactured by adding a proper amount of the above ceramic composition thereto.

As the metallic ions of silver, copper, and zinc were found to have a disinfectant property, they have been used as disinfectants in a state of organic and/or inorganic metal salt. Moreover, the metallic salts of the above mentioned metals have been known to have especially superior disinfectant property for a Escherichia coli, *Staphylococcus aureus*, bacillus, mold, tinea, vibrio, salmonella, and carious tooth bacteria.

Until the present, the above metals were typically used in a liquid state, for example, silver ions were used as a disinfectant and/or germicide in a silver nitrate solution. However, since a liquid state is not easily dealt with and does not show a stable effect and an inferior heat resistance property, the utilization of it is inevitablely restricted.

In order to solve the above problem, French Patent No. 1061158 and Japanese Patent No. 63-54013 have developed a method for using the above mentioned disinfectant metals in a state of a metallic zeolite. This is acquired by substituting the above metallic ions with cation($Na^+$) of zeolite because natural and/or artificial zeolite has an ion-exchanging property. The metallic zeolite thus made has a relatively improved heat resistance and stability.

However, the above method has a serious problem in that it has a degraded disinfectant property due to the fact that it is likely to have damage to its porosity when being dried and substituted. Another problem of the above method is that the control of the surface area and the mole rate of $SiO_2$ or $Al_2O_3$ is difficult. It is still another problem of the above method that when the absorption ratio of zeolite itself meets the saturated level, e.g. the state of absorption incapability, the degradation effect is unavoidable.

Last but not least, it is also a serious problem of the above method that it has an inferior compatibility with living things.

SUMMARY OF THE INVENTION

Keeping in mind the defects of the prior method, it is an object of the present invention to provide a ceramic material which can be easily manufactured, has a stable disinfectant property, catches heavy metals which are harmful to human body, and radiates far infra-red rays which have a positive influence on living things.

It was discovered by the inventor that the above objectives may be achieved by using a material made from the burning of the bone of vertebrate animals such as cows, pigs, etc. or a compound containing phosphorus and alkaline earth metal such as artificial apatite, as a base material, and reacting these base material with metals with disinfectant and harmless property such as silver, copper, or zinc.

DETAILED DESCRIPTION OF THE INVENTION

Examples of the base materials which can be used for the present invention are compounds containing alkaline earth metal and phosphorus such as granulated bone of vertebrate animals or crustacea burnt at a high temperature, fossils of vertebrate animals, artificial apatite, phosphate calcium ore, TCP(tricalcium phosphate), $Mg_3(PO_4)_2.5H_2O$, $MgO.3SiO_2.xH_2O$, and $Sr(C_3H_5OH)_2.3H_2O$. However, compounds containing calcium and phosphorus are most preferred in that they have disinfectant properties against harmful bacteria as by themselves. Moreover, these compounds activate beneficial bacteria for the human body. On the other hand, compounds containing barium or magnesium have a disadvantage in that they are easily dissolved in water.

Using the base materials manufactured as above, by reacting various kinds of metals with disinfectant and harm free properties such as silver, copper, or zinc, a disinfectant ceramic material of the present invention can be obtained. Here, the ionic tendencies of the above described metals (silver, copper, and zinc) are lower than those of alkaline earth metals. Accordingly if these metals are reacted with compounds containing alkaline earth metals, a substitution reaction between them is expected.

Although the metal amount used is dependant on the kind of the base materials used, if using granulated bone as the base materials, then the proper amount of metal is less than 25 wt % of the dry weight of the base material when silver is used, and 10 wt % when copper or zinc is used. When exceeding the above described amount, it is likely that the above metallic ions will come out more than those required for the human body and thus, they can have a negative influence on it. Also, since the ratio of alkaline earth metals which cannot be substituted become relatively small, the capability of catching heavy metals, one of the primary objects of the present invention, becomes insufficient.

In the case where disinfectant metals have a substituting reaction with the base materials in accordance with the above mentioned ratio, the ceramic materials thus made are capable of having a disinfectant property due to the disinfectant metals substituted. At the same time, alkaline earth metals remaining non-substituted can catch harmful ions of heavy metals such as $Hg^{}$, $Pb^{}$, and $Cd^{**}$ by substitution and furthermore, they can get rid of harmful anions such as $Cl^-$, and $F^-$.

The examples of the base materials which are most preferable for using as containers or wrappers for food are compounds containing calcium and phosphorous such as TCP, artificial apatite, or $Ca_{10}(PO_4)_6(OH)_2$ (which is a primary composition of granulated bone of vertebrate animals).

However, the artificial apatite is too expensive, and TCP has an inferior affinity with the human body compared to the granulated bone. For base materials other than the food storing container or other kitchen goods, TCP or phosphate calcium ore can be used as base materials.

When bone of a vertebrate animal is burnt at a temperature of 1000° C., most of the organic and inorganic substances evaporate, and the remains after the evaporation become porous materials which are able to absorb impurities and heavy metals with ease. Thus they can promote the effect of catching heavy metals. When granulated into very fine particles having an average particle diameter less than 0.2 μm, the porous materials comes to have a specific surface area of roughly 200 m²/g. Since, these granulated particles have a property of radiating far infra-red rays, they can also be used as the materials for making a far infra-red ray radiating ceramic material.

Also, in the case of using the base materials as an artificial bone or tooth for man, by adding a proper amount of the above disinfectant metals, the occurrence of inflammation or carious tooth after an operation can be remarkably reduced. Additionally, a container for food made of the base materials containing calcium salt, such as the above granulated bone, may help water or wine to become more tasteful by eluting small quantities of calcium which may supply a human body with calcium ions, which are likely to be in short supply.

DESCRIPTION OF THE PREFERRED EMBODIMENT

Example 1

Make a 1,000 g of bone powder by burning the bone of a cow at 1000° C., and then granulate it into fine powder of 0.1 μm particle diameter. Make a solution by dissolving 33 g of $AgNO_3$ with 1,500 ml of water. Mix the above bone powder with the above solution, stir the mixture for 2 hours at a temperature of 25° C., precipitate it, do away with liquid matter, add 5,000 ml of water, stir it for 1 hour, and pick up the remaining liquid matter. Continue washing until no more white deposits are found when adding a few drops of 0.1N HCl to the liquid matter obtained as above. Thereafter, precipitate the solid matter and desiccate it by applying hot air of 100° C., and thus the resulting C1 is acquired.

Example 2

Make a solution by dissoluting 13 g of $CuSO_4$ with 1,500 ml of water. Mix 1,000 g of the bone powder obtained in example 1 with the above solution, stir the mixture for 3 hours, and precipitate it. Continue washing until no more reddish brown reaction is found when adding a few drops of $K_4Fe(CN)$ to the liquid matter of the above mixture, and then precipitate the solid matter. Desiccate the solid matter thus made by applying hot air of 100° C., and thus the resulting C2 is acquired.

Example 3

Make a solution by dissoluting 11 g of $ZnCl_2$ with 2,000 ml of water. Mix 1,000 g of the bone powder obtained in example 1 with the above solution, stir up the mixture for 3 hours, and precipitate it. Continue washing until no more white deposits are found when adding a few drops of 0.1N $AgNO_3$. Thereafter, desiccate the solid matter by applying 100° C. of hot air, and thus the resulting C3 is acquired.

Test 1

Taking the above 3 substances, C1, C2, and C3, mix each one with polypropylene at a ratio of 2 wt % C1 (C2, or C3) Taking these mixtures, make 3 containers for food by injection molding at 200° C. Pick up the 3 containers and take a piece from each of them to be used as samples (Now labeled D1, D2, and D3)

Results 1

Far infra-red ray radiating ratios of each sample D1, D2, and D3 measured at a wavelength of 10 μm are as follows:

| Sample | D1 | D2 | D3 |
| --- | --- | --- | --- |
| Radiation ratio | 93 | 90 | 91 |

Test 2

Going back to the 3 substances, C1, C2, and C3, mix each one with a conventional sizing agent at a ratio of 3 wt % C1 (C2 or C3). Make 3 different wall papers by sizing each of the mixtures obtained above, pick up the 3 wall papers and take a piece from each of them to be used as samples (Now labled E1, E2, and E3.) Also, prepare a sample of wallpaper obtained by the above sizing agent alone, and label it as E4.

Results 2

In order to test the antibacterial property of each sample, E1, E2, E3, and E4 they are left in a room where sun light is blocked and the relative humidity is 90%, for half a month. Thereafter, the occurrence of mold in each of the samples was investigated and is shown in the following table.

| Sample | E1 | E2 | E3 | E4 |
| --- | --- | --- | --- | --- |
| Occurrence | Not Occurred | Occurred little | Not Occurred | Occurred severely |

In sample E2, the occurring of mold started a little after 10 days but did not increase, while in sample E4, mold started occurring after 7 days and continued to increase. In sample E1 and E3, no occurrence of mold was found for the entire 15 days.

What is claimed is:

1. A disinfectant composition manufactured by substituting an amount of the alkaline earth metal in powdered vertebrate animal bone with an amount of silver, copper or zinc effective to render the composition antibacterial and non-toxic to a human body.

2. A disinfectant composition of claim 1, when the animal bone was previously burned.

3. A disinfectant composition of claim 2, wherein the animal bone was previously burned at a temperature of about 1000° C.

4. An article comprising a disinfectant composition that is manufactured by substituting an amount of the alkaline earth metal in powdered vertebrate animal bone with an amount of silver, copper or zinc effective to render the composition antibacterial and non-toxic to a human body.

5. An article of claim 4, wherein the disinfectant composition comprises from about 0.1% to about 20% by weight of the article.

6. A method of making a disinfectant composition which comprises:
   a. providing powdered vertebrate animal bone;
   b. contacting the powdered animal bone with an amount of silver, copper or zinc effective to substitute for the alkaline earth metal in the powdered animal bone, the substitution being in an amount effective to render the composition antibacterial and non-toxic to a human body.

7. The method of claim 6 wherein the animal bone was previously burned.

* * * * *